United States Patent
Chen et al.

(10) Patent No.: US 11,793,470 B2
(45) Date of Patent: Oct. 24, 2023

(54) METHOD AND DEVICE FOR CALIBRATING PHYSIOLOGICAL READINGS, ELECTRONIC DEVICE USING METHOD, AND NON-TRANSITORY STORAGE MEDIUM

(71) Applicant: Jiangyu Kangjian Innovation Medical Technology(Chengdu) Co., Ltd, Chengdu (CN)

(72) Inventors: Cheng Chen, Shenzhen (CN); Ping-Hao Liu, New Taipei (TW); Neng-De Xiang, Shenzhen (CN); Ming-Shun Hu, Shenzhen (CN)

(73) Assignee: Jiangyu Kangjian Innovation Medical Technology(Chengdu) Co., Ltd, Chengdu (CN)

( * ) Notice: Subject to any disclaimer, the term of this patent is extended or adjusted under 35 U.S.C. 154(b) by 367 days.

(21) Appl. No.: 17/029,343

(22) Filed: Sep. 23, 2020

(65) Prior Publication Data

US 2021/0330268 A1    Oct. 28, 2021

(30) Foreign Application Priority Data

Apr. 23, 2020   (CN) .................. 202010328240.X (51) Int. Cl.
*A61B 5/021*   (2006.01)
*A61B 5/1455*   (2006.01)
(Continued)

(52) U.S. Cl.
CPC ............ *A61B 5/7267* (2013.01); *A61B 5/021* (2013.01); *A61B 5/1455* (2013.01);
(Continued)

(58) Field of Classification Search
CPC ... A61B 5/7267; A61B 5/021; A61B 5/14532; A61B 5/1455; A61B 5/681;
(Continued)

(56) References Cited

U.S. PATENT DOCUMENTS

| | | | | |
|---|---|---|---|---|
| 2015/0289820 | A1* | 10/2015 | Miller | ................ A61B 5/02438 600/300 |
| 2019/0008461 | A1 | 1/2019 | Gupta et al. | |
| 2021/0298648 | A1* | 9/2021 | Hefner | ................ A61B 5/1495 |

FOREIGN PATENT DOCUMENTS

| | | |
|---|---|---|
| CN | 1548005 A | 11/2004 |
| CN | 103479339 A | 1/2014 |

(Continued)

OTHER PUBLICATIONS

Ghosh et al. (An improved model averaging scheme for logistic regression. J Multivar Anal. 2009;100(8):1670-1681. doi: 10.1016/j.jmva.2009.01.006. PMID: 20216921; PMCID: PMC2834220.) (Year: 2009).*

(Continued)

*Primary Examiner* — Daniel R Miller
*Assistant Examiner* — Christian T Bryant
(74) *Attorney, Agent, or Firm* — ScienBiziP, P.C.

(57) ABSTRACT

A method for calibrating measurements of human physiological state applied on an electronic device couples the device to at least one uncalibrated measurement device, worn or placed. Readings of a physiological state are collected by the uncalibrated measurement device and the readings are input into a model for calibration. A sub-module corresponding to the type of reading, for blood pressure or heart rate for example, is called up from the calibration model and a regression algorithm is applied to the calibration model to generate a calibrated reading, each sub-module in the model corresponding to one type of reading. The method also outputs calibrated physiological measurements by the called-up sub-module. A related electronic device and a non-transitory storage medium are also disclosed.

14 Claims, 4 Drawing Sheets

(51) Int. Cl.
    *A61B 5/0205*     (2006.01)
    *A61B 5/00*     (2006.01)
    *A61B 5/145*     (2006.01)

(52) U.S. Cl.
    CPC .......... *A61B 5/14532* (2013.01); *A61B 5/681* (2013.01); *A61B 5/0205* (2013.01); *A61B 5/14542* (2013.01); *A61B 5/7221* (2013.01); *A61B 5/7235* (2013.01); *A61B 2560/0223* (2013.01)

(58) Field of Classification Search
    CPC .......... A61B 2560/0223; A61B 5/7221; A61B 5/0205; A61B 5/14542; A61B 5/7235
    See application file for complete search history.

(56) References Cited

FOREIGN PATENT DOCUMENTS

| | | | |
|---|---|---|---|
| CN | 109872820 A | 6/2019 | |
| WO | WO-2021026399 A1 * | 2/2021 | ........... A61B 5/1118 |

OTHER PUBLICATIONS

Kotsiantis et al. (Bagged Averaging of Regression Models, Mathematics University of Patras, Greece, pp. 53-60, IFIP International Federation for Information Processing, vol. 204, Artificial Intelligence Applications and Innovations, eds, 2006) (Year: 2006).*

Mamun (Model Averaging: A Robust Way to Deal with Model Uncertainty, Towards Data Science, Dec. 7, 2019) (Year: 2019).*

* cited by examiner

METHOD AND DEVICE FOR CALIBRATING PHYSIOLOGICAL READINGS, ELECTRONIC DEVICE USING METHOD, AND NON-TRANSITORY STORAGE MEDIUM

FIELD

The subject matter herein generally relates to human health and particularly, to a method and device for calibrating physiological measurements, an electronic device using the method, and a non-transitory storage medium.

BACKGROUND

Many physiological parameters exist in relation to human health. The parameters may include, for example, blood pressure value, blood oxygen value, blood fat value, blood glucose value, heart rate value, and so on. When any reading exceeds or does not match a standard value, a medical treatment can be administered or taken, thus a risk of worse illness can be reduced. A number of wearable measurement devices are employed to monitor and measure the physiological state in real time, but the measurements data is not calibrated and may be inaccurate.

BRIEF DESCRIPTION OF THE DRAWINGS

Many aspects of the disclosure can be better understood with reference to the following drawings. The components in the drawings are not necessarily drawn to scale, the emphasis instead being placed upon clearly illustrating the principles of the disclosure. Moreover, in the drawings, like reference numerals designate corresponding parts throughout the several views.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The present disclosure, referencing the accompanying drawings, is illustrated by way of examples and not by way of limitation. It should be noted that references to "an" or "one" embodiment in this disclosure are not necessarily to the same embodiment, and such references mean "at least one." The term "and/or" includes any and all combinations of one or more of the associated listed items.

Figure 1:
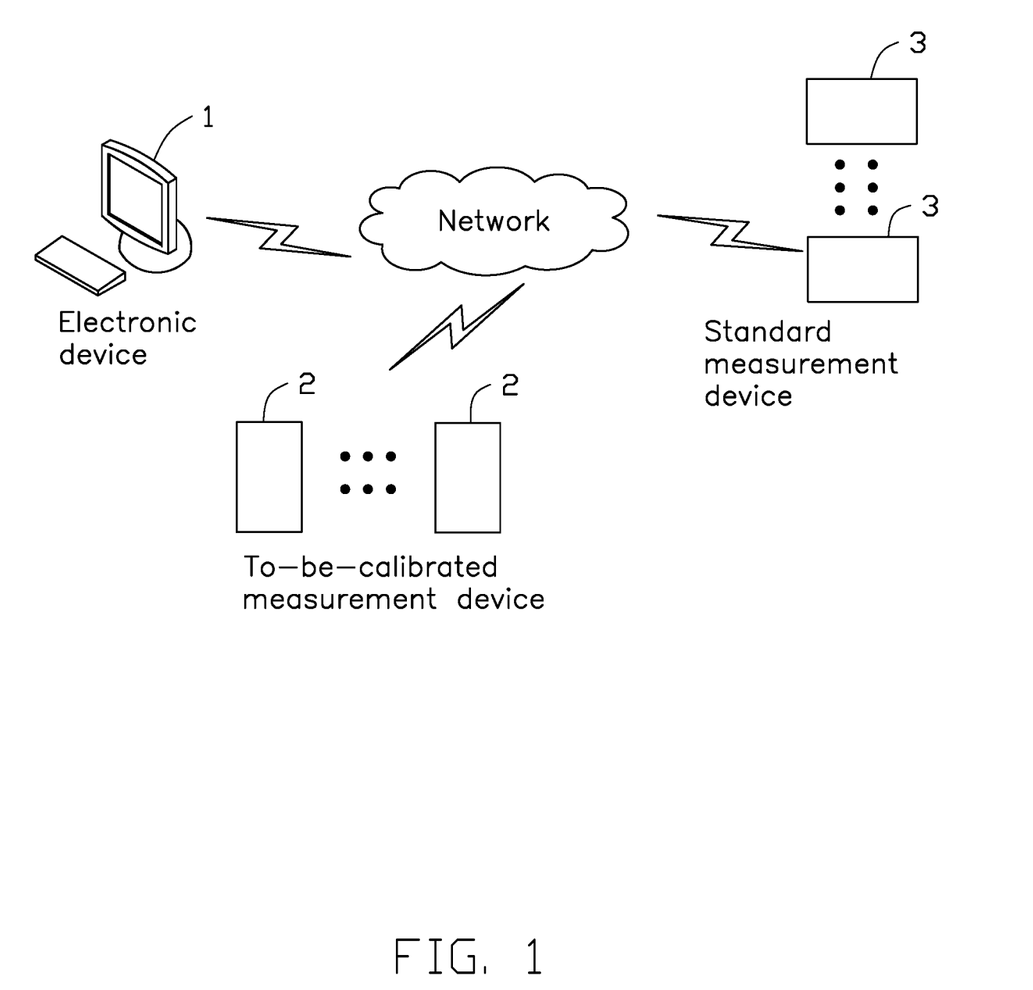
FIG. 1 is a view of a first embodiment of an application environment of a method for calibrating physiological measurements.

FIG. 1 is a view of a first embodiment of an application environment of a method for calibrating measurements of human physiology (hereinafter method). The method is applied on an electronic device 1. The electronic device 1 is coupled to at least one uncalibrated measurement device 2 and at least one standard measurement device 3 via a network. The network can be a wired network or a wireless network. The wireless network can be, for example, a radio network, a WIFI network, a cellular network, a satellite network, a broadcast network, or the like.

The electronic device 1 may be an electronic device with a software for calibrating measurements of physiology. The electronic device can be, for example, a personal computer, a smart phone, or the like.

The uncalibrated measurement device 2 can be a portable electronic device for measuring and taking readings of a physiological state. The readings can relate to blood pressure value, blood oxygen value, blood fat value, blood glucose value, heart rate value, and so on. The portable electronic device (device 2) can be a smart bracelet, smartwatch, a portable oximeter, a portable scale, or the like.

The standard measurement device 3 can be an electronic device used for medical purposes. The device 3 can contain medical information as to blood pressure value, blood oxygen value, blood fat value, blood glucose value, heart rate value, and so on. The medical electronic device can be a medical sphygmomanometer, a medical blood glucose meter, a device for detecting heart rate, or the like.

Figure 2:
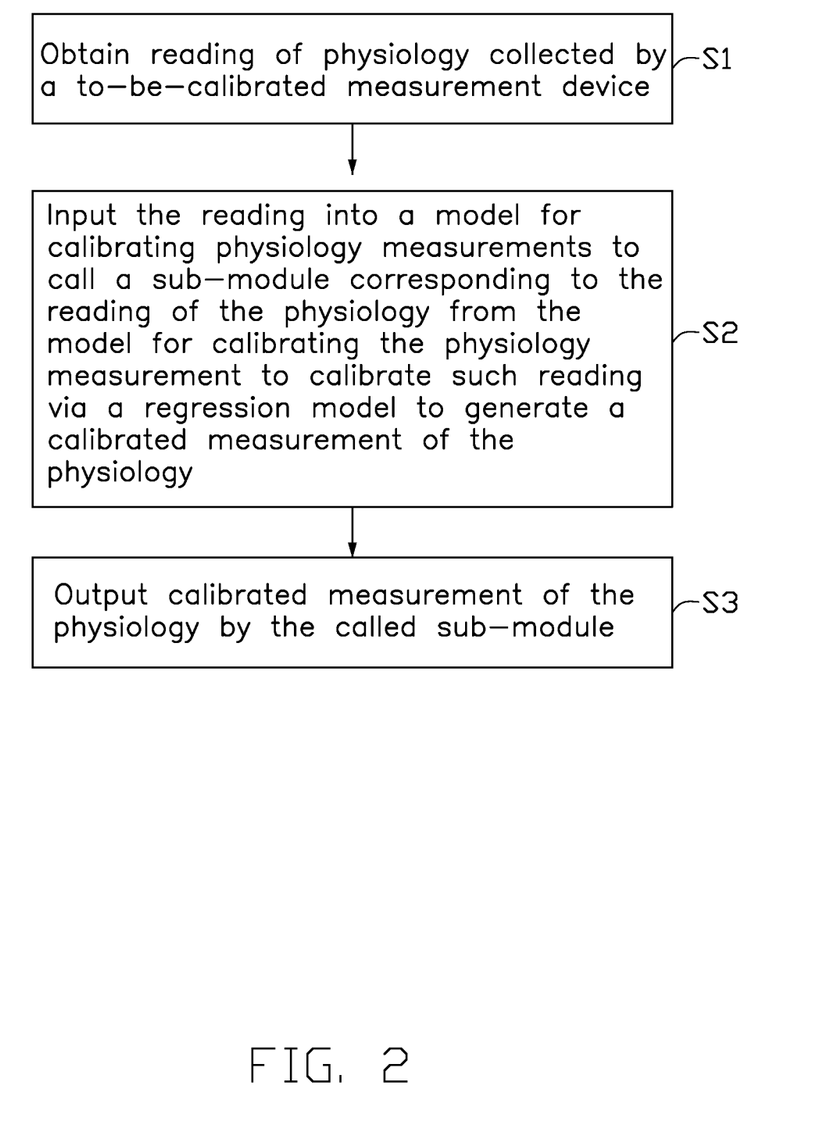
FIG. 2 is a flowchart of a second embodiment of a method.

FIG. 2 is a flowchart of a second embodiment of a method for calibrating measurements of physiological state. A sequence of blocks of the flowchart can be altered and some blocks of the flowchart can be omitted according to needs. The method begins at block S1.

At block S1, obtaining physiological reading collected by an uncalibrated measurement device.

The reading include, but is not limited to, any one of a group of blood pressure value, blood oxygen value, blood fat value, blood glucose value, heart rate value, and the like.

A step of obtaining physiological reading collected by an uncalibrated measurement device can include receiving a reading transmitted by the at least one uncalibrated measurement device via a network or receiving a reading as a direct input collected by the at least one uncalibrated measurement device.

At block S2, inputting the reading into a model for calibration to generate a calibrated physiological measurement whereby a sub-module corresponding to the reading is called from the model for calibration, and the sub-module is for calibrating such reading via a regression algorithm.

In the embodiment, each sub-module in the model corresponds to one physiological reading.

The model for calibration contains different sub-modules corresponding to a detail content of the readings. For example, a first sub-module corresponds to the blood pressure value, a second sub-module corresponds to the blood oxygen value, a third sub-module corresponds to the blood glucose value, a fourth sub-module corresponds to the heart rate value, a fifth sub-module corresponds to the blood fat value, and so on.

The method further includes generating the sub-modules in the model for calibration. A step of generating the sub-modules in the model for calibration includes a step a1 and a step a2.

The step a1 includes selecting at least two regression algorithms selected from preset sorting algorithms, to train and to create at least two modules for a same kind of reading of the physiological state. The preset sorting algorithms includes a linear regression, a nonlinear regression, a locally weighted regression, and so on.

The step a2 includes averaging the at least two created modules to generate the sub-module in the model for calibration.

In the embodiment, the step a1 includes a step b1, a step b2, a step b3, a step b4, a step b5, a step b6, and a step b7. The step b1 includes obtaining a number of sets of sample data. The sample data includes physiological measurements of a user and standard physiological information. In this situation, the physiological measurements are taken by the at least one uncalibrated measurement device, and the standard physiological information is contained within or taken by the at least one standard measurement device. The step b2 includes dividing the sample data into a training set and a validation set. The step b3 includes establishing an analysis model based on a regression algorithm. The step b4 includes training the analysis model via the training set, where an input of the analysis model is the physiological measurements in the training set, and an output of the analysis model is the standard physiological information in the training set.

The step b5 includes validating the trained analysis model via the validation set to generate a predicted accuracy of the trained analysis model.

The step b6 includes determining whether the predicted accuracy of the trained analysis model is less than a preset threshold.

The step b7 includes determining the trained analysis model as being the module if the predicted accuracy of the trained analysis model is not less than the preset threshold.

The step a1 further includes a step b8, a step b9, a step b10, a step b11, and a step b12. The step b8 includes adjusting the regression algorithm of the analysis model, or the number of the samples in the training set, or the regression algorithm of the analysis model and the number of the samples in the training set, to resume training the analysis model via the training set if the predicted accuracy of the trained analysis model is less than the preset threshold.

The step b9 includes validating the resumed trained analysis model via the validation set to resume generating a predicted accuracy of the resumed trained analysis model.

The step b10 includes determining whether the resumed predicted accuracy of the resumed trained analysis model is less than the preset threshold.

The step b11 includes determining the resumed trained analysis model as being the module if the resumed predicted accuracy of the resumed trained analysis model is not less than the preset threshold.

The step b12 includes continuing to adjust the regression algorithm of the analysis model, or the number of the samples in the training set, or the regression algorithm of the analysis model and the number of the samples in the training set, to resume training the analysis model via the training set, and to validate the resumed trained analysis model via the validation set to resume generating a predicted accuracy of the resumed trained analysis model until the predicted accuracy is not less than the preset threshold if the resumed predicted accuracy of the resumed trained analysis model is less than the preset threshold.

A step of obtaining a number of sets of sample data includes a step c1 and a step c2. The step c1 includes obtaining a number of sets of physiological measurements taken by the at least two uncalibrated measurement devices and a number of sets of standard physiological information measured by the at least two standard measurement devices.

The step c2 includes combining the sets of physiological measurements and the sets of standard physiological information according to codes of the uncalibrated measurement devices and codes of the standard measurement devices to obtain a combination of each physiological measurement and all the standard physiological information, or a combination of each standard physiological information and all the physiological measurements.

For example, to reduce differences between the devices, quantity m of uncalibrated measurement devices and quantity n of standard measurement devices are selected to be matched and measured, thus m*n matchings are generated. To keep a consistency of the sample data, the uncalibrated measurement devices and the standard measurement devices should be keep at a same state, for example a first uncalibrated measurement device measures the blood pressure value, and a first standard measurement device measures the blood pressure value. To cover all possible data, the method measures different people with different states of health and in different environments. In the embodiment, the accuracy of the model becomes greater when the sample data is more extensive.

At block S3, outputting calibrated physiological measurement by the sub-module which is called up.

In the embodiment, the method includes outputting calibrated physiological measurement by the sub-module which is called up if the calibrated physiological measurement is within a preset threshold range.

In the embodiment, before outputting calibrated physiological measurement by the sub-module which is called up if the calibrated physiological measurement is within a preset threshold range, the method further includes a step d1 and a step d2. The step d1 includes comparing the calibrated physiological measurement with the preset threshold range. The step d2 includes generating a prompt if the calibrated physiological measurement is outside of the preset threshold range. The prompt can be output via email, message, instant messaging software, or the like.

Figure 3:
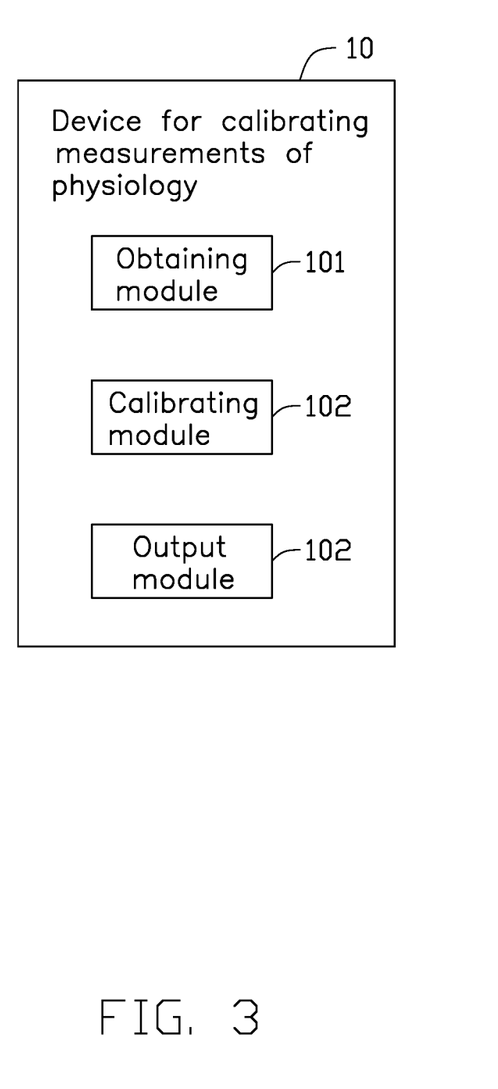
FIG. 3 is a block diagram of an embodiment of a device for calibrating measurements of physiology.
Figure 4:
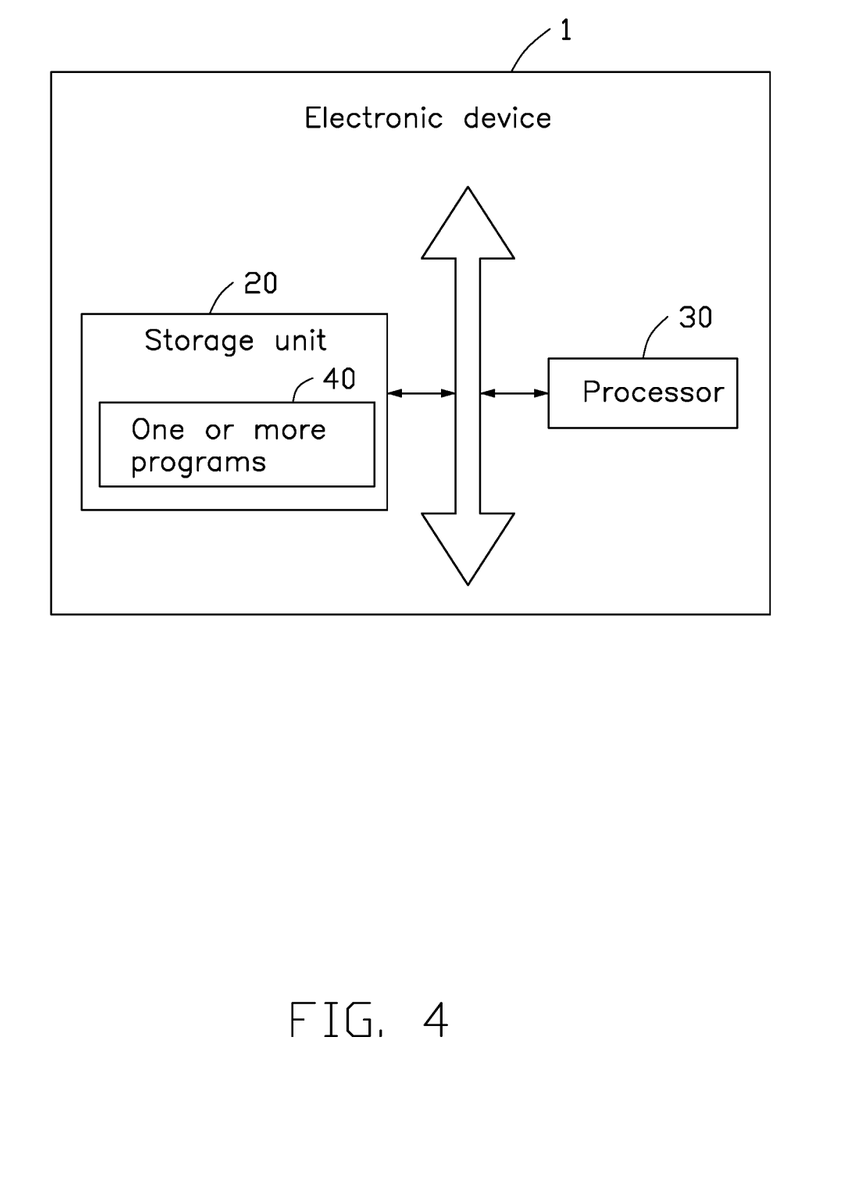
FIG. 4 is a block diagram of another embodiment of an electronic device.

FIG. 2 describes the method in detail. With reference to FIGS. 3-4, the function module of a software to achieve the method and a hardware device to achieve the method will be described.

The embodiment is to illustrate the disclosure and not limit the disclosure.

FIG. 3 is a block diagram of an embodiment of a device for calibrating measurements of physiology. In some embodiments, the device for calibrating measurements of physiology (hereinafter device 10) is applied on an electronic device. The electronic device is coupled to a number of terminals of the user. The device 10 includes a number of function modules consisting of a series of program instruction segments. The program instruction of each program segment in the device 10 can be stored in a storage unit of the electronic device and executed by the at least one processor to accomplish a function of calibrating measurements of physiology.

The device 10 can be divided into one or more modules/units to accomplish the purpose of the present disclosure. Referring to FIG. 3, the function modules can include an obtaining module 101, a calibrating module 102, and an output module 103. The one or more modules/units can be a series of program instruction segments which can perform specific functions and be executed by the at least one processor. The one or more modules/units can be stored in the storage unit.

The obtaining module 101 obtains physiological reading collected by an uncalibrated measurement device.

The reading include, but is not limited to, any one of a group of blood pressure value, blood oxygen value, blood fat value, blood glucose value, heart rate value, and the like.

The module can receive the reading transmitted by the at least one uncalibrated measurement device via a network or receive an input of a direct reading collected by the uncalibrated measurement device, to obtain the reading.

The calibrating module 102 inputs the reading into a model for calibration to call up a sub-module corresponding to the reading from the model for calibration, to calibrate the particular reading via a regression algorithm to generate a calibrated physiological measurement.

In the embodiment, each sub-module in the model corresponds to one type of reading.

The model for calibration contains different sub-modules corresponding to a detail content of the reading. For example, a first sub-module corresponds to the blood pressure value, a second sub-module corresponds to the blood oxygen value, a third sub-module corresponds to the blood glucose value, a fourth sub-module corresponds to the heart rate value, a fifth sub-module corresponds to the blood fat value, and so on.

The calibrating module 102 is further configured to generate the sub-modules in the model for calibration. The module to generate the sub-modules in the model for calibration includes a module a1 and a module a2.

The module a1 is configured to select at least two regression algorithms selected from preset sorting algorithms, to train and to create at least two modules for a same kind of reading of the physiological state. The preset sorting algorithms includes a linear regression, a nonlinear regression, a locally weighted regression, and so on.

The module a2 is configured to average the at least two created modules to generate the sub-module in the model for calibration.

In the embodiment, the module a1 includes a module b1, a module b2, a module b3, a module b4, a module b5, a module b6, and a module b7. The module b1 is configured to obtain a number of sets of sample data. The sample data includes physiological measurements of the user and standard physiological information. The physiological measurements are taken by the at least one uncalibrated measurement device, and the standard physiological information is contained within or taken by the at least one standard measurement device. The module b2 is configured to divide sample data into a training set and a validation set. The module b3 is configured to establish an analysis model based on a regression algorithm. The module b4 is configured to train the analysis model via the training set, where an input of the analysis model is the physiological measurements in the training set and an output is the standard physiological information in the training set.

The module b5 is configured to validate the trained analysis model via the validation set to generate a predicted accuracy of the trained analysis model.

The module b6 is configured to determine whether the predicted accuracy of the trained analysis model is less than a preset threshold.

The module b7 is configured to determine the trained analysis model as being the module if the predicted accuracy of the trained analysis model is not less than the preset threshold.

The module a1 further includes a module b8, a module b9, a module b10, a module b11, and a module b12. The module b8 is configured to adjust the regression algorithms of the analysis model, or the number of the samples in the training set, or the regression algorithms of the analysis model and the number of the samples in the training set, to resume training the analysis model via the training set if the predicted accuracy of the trained analysis model is less than the preset threshold.

The module b9 is configured to validate the resumed trained analysis model via the validation set to resume generating a predicted accuracy of the adjusted analysis model based on regression algorithms.

The module b10 is configured to determine whether the resumed predicted accuracy of the resumed trained analysis model is less than the preset threshold.

The module b11 is configured to determine the resumed trained analysis model as being the module if the resumed predicted accuracy of the resumed trained analysis model is not less than the preset threshold.

The module b12 is configured to continue to adjust the regression algorithm of the analysis model, or the number of the samples in the training set, or the regression algorithm of the analysis model and the number of the samples in the training set, to resume training the analysis model via the training set, and to validate the resumed trained analysis model via the validation set to resume generating a predicted accuracy of the resumed trained analysis model until the predicted accuracy is not less than the preset threshold if the resumed predicted accuracy of the resumed trained analysis model is less than the preset threshold.

The module to obtain a number of sets of sample data includes a module c1 and a module c2. The module c1 is configured to obtain a number of sets of physiological measurements taken by the at least two uncalibrated measurement devices and a number of sets of standard physiological information measured by the at least two standard measurement devices.

The module c2 is configured to combine the sets of physiological measurements and the sets of standard physiological information according to codes of the uncalibrated measurement devices and codes of the standard measurement devices to obtain a combination of each physiological measurement and all the standard physiological information, and a combination of each standard physiological information and all the physiological measurements.

For example, to reduce differences between the devices, quantity m of uncalibrated measurement devices and quantity n of standard measurement devices are selected to be matched and measured, thus m*n matchings are generated. To keep a consistency of the sample data, the uncalibrated measurement devices and the standard measurement devices should be keep at a same state, for example a first uncalibrated measurement device measures the blood pressure value, and a first standard measurement device measures the blood pressure value. To cover all possible data, the method measures different people with different states of health and in different environments. In the embodiment, the accuracy of the model becomes greater when the sample data is more extensive.

The output module 103 is configured to output calibrated physiological measurement by the sub-module which is called up.

In the embodiment, the output module 103 is configured to output calibrated physiological measurement by the sub-module which is called up if the calibrated physiological measurement is within a preset threshold range.

In the embodiment, the output module 103 is further configured to compare the calibrated physiological measurement with the preset threshold range, and generate a prompt if the calibrated physiological measurement is outside of the preset threshold range. The prompt can be output via email, message, instant messaging software, or the like.

FIG. 4 is a block diagram of another embodiment of an electronic device.

The electronic device 1 can include a storage unit 20, at least one processor 30, and one or more programs 40 stored in the storage unit 20 and can be run on the at least one processor 30, for example program for calibrating measurements of physiology. The at least one processor 30 can execute the one or more programs 40 to accomplish the steps of the exemplary method for calibrating measured physiology parameter, for example block S1~block S3 of the FIG. 2, or the at least one processor 30 can execute the one or more modules/units to accomplish the calibration of measurements in physiology, for example module 101~103 of the FIG. 3.

The one or more programs 40 can be divided into one or more modules/units. The one or more modules/units can be stored in the storage unit 20 and executed by the at least one processor 30 to accomplish the object of the present disclosure. The one or more modules/units can be a series of program instruction segments which can perform specific functions, the instruction segment is configured to describe the execution process of the one or more programs 40 in the electronic device 1. For example, the one or more programs can be divided into the obtaining module, the calibrating module, and the output module of FIG. 3.

The electronic device 1 can be any suitable electronic device, for example, a personal computer, a tablet computer, a mobile phone, a PDA, or the like. A person skilled in the art knows that the device in FIG. 4 is only an example, and is not to be considered as limiting the electronic device 1, another electronic device 1 may include more or fewer parts than as described, or combine certain parts differently, or include different parts, such as the electronic device 1 also including one or more input and output devices, one or more network access devices, one or more display devices, and so on.

The at least one processor 30 can be one or more central processing units, or it can be one or more other universal processors, digital signal processors, application specific integrated circuits, field-programmable gate arrays, or other programmable logic devices, discrete gate or transistor logic, discrete hardware components, and so on. The at least one processor 30 can be a microprocessor or the at least one processor 30 can be any regular processor, or the like. The at least one processor 30 can be a control center of the electronic device 1, using a variety of interfaces and lines to connect various parts of the entire electronic device 1.

The storage unit 20 stores the one or more programs and/or modules/units. The at least one processor 30 can run or execute the one or more programs and/or modules/units stored in the storage unit 20, call out the data stored in the storage unit 20, and accomplish the various functions of the electronic device 1, for example apply the method hereinbefore described. The storage unit 20 may include a program area and a data area. The program area can store an operating system, and applications that are required for the at least one function, such as sound playback features, images playback functions, and so on. The data area can store data created according to the use of the electronic device 1, such as video data, audio data, photobook data, and so on. In addition, the storage unit 20 can include random access memory and non-transitory storage medium, such as hard disk, memory, plug-in hard disk, smart media card, secure digital, flash card, at least one disk storage device, flash memory, or other transitory storage medium.

If the integrated module/unit of the electronic device 1 is implemented in the form of or by means of a software functional unit and is an independent product as sold or used, all parts of the integrated module/unit of the electronic device 1 may be stored in a computer-readable storage medium. The electronic device 1 can use one or more programs to control the related hardware to accomplish all parts of the method of this disclosure. The one or more programs can be stored in a computer-readable storage medium. The one or more programs can be accomplish a process in the exemplary method when executing by the at least one processor. The one or more stored programs can include program code. The program code can be in the form of source code, object code, executable code file, or in some intermediate form. The computer-readable storage medium may include any entity or device capable of recording and carrying the program codes, recording media, USB flash disk, mobile hard disk, disk, computer-readable storage medium, read-only memory, Random access memory, electrical carrier signals, telecommunications signals, and software distribution package. The content stored in the computer-readable storage medium can be increased or decreased in accordance with legislative requirements and regulations of patent practice jurisdictions, for example, in some jurisdictions, legislation and patent practice stipulate that a computer-readable storage medium does not include electrical carrier signals or telecommunications signals.

In the present disclosure, it should be understood that the disclosed methods and electronic devices can be employed or achieved in other ways. The electronic device exemplified is only illustrative. For example, the divisions of the unit are only divisions according to logical function, and an actual implementation may have divisions of a different manner.

In addition, various functional units in the various embodiments of the disclosure may be integrated in one processing unit, each unit may be physically separated, or two or more units may be integrated in one unit. The above-mentioned integrated unit can be realized in the form of hardware or software functional unit.

It should be emphasized that the above-described embodiments of the present disclosure, including any particular embodiments, are merely possible examples of implementations, set forth for a clear understanding of the principles of the disclosure. Many variations and modifications can be made to the above-described embodiment(s) of the disclosure without departing substantially from the spirit and principles of the disclosure. All such modifications and variations are intended to be included herein within the scope of this disclosure and protected by the following claims.

What is claimed is:

1. A method for calibrating measurements of physiology applied on an electronic device, the electronic device being communicationally coupled to at least one uncalibrated measurement device, the method comprising:
obtaining physiological reading collected by an uncalibrated measurement device;
inputting the reading into a model for calibration to generate a calibrated physiological measurement whereby a sub-module corresponding to the reading is called from the model for calibration and the sub-module is for calibrating the reading via a regression algorithm, where each sub-module in the model corresponds to one physiological reading;
outputting calibrated physiological measurement by the called sub-module;

wherein the method further comprises:
selecting at least two regression algorithms selected from preset sorting algorithms, to train and to create at least two modules for a same kind of reading of the physiological state;
averaging the at least two created modules to generate the sub-module in the model for calibration;

wherein selecting at least two regression algorithms selected from preset sorting algorithms, to train and to create at least two modules for a same kind of reading of the physiological state comprises:
obtaining a plurality of sets of sample data, the sample data comprises physiological measurements of a user and standard physiological information, where the physiological measurements are taken by the at least one uncalibrated measurement device, and the standard physiological information is contained within or taken by the at least one standard measurement device;
dividing the sample data into a training set and a validation set;
establishing an analysis model based on a regression algorithm;
training the analysis model via the training set, where an input of the analysis model is the physiological measurements in the training set and an output of the analysis model is the standard physiological information in the training set;
validating the trained analysis model via the validation set to generate a predicted accuracy of the trained analysis model;
determining whether the predicted accuracy of the trained analysis model is less than a preset threshold;
determining the trained analysis model as being the module if the predicted accuracy of the trained analysis model is not less than the preset threshold.

2. The method according to claim 1, wherein the method further comprises:
comparing the calibrated physiological measurement with a preset threshold range;
generating a prompt if the calibrated physiological measurement is outside of the preset threshold range.

3. The method according to claim 1, wherein the method further comprises:
adjusting the regression algorithm of the analysis model, or the number of the samples in the training set, or the regression algorithm of the analysis model and the number of the samples in the training set, to resume training the analysis model via the training set if the predicted accuracy of the trained analysis model is less than the preset threshold;
validating the resumed trained analysis model via the validation set to resume generating a predicted accuracy of the resumed trained analysis model;
determining whether the resumed predicted accuracy of the resumed trained analysis model is less than the preset threshold;
determining the resumed trained analysis model as being the module if the resumed predicted accuracy of the resumed trained analysis model is not less than the preset threshold;
continuing to adjust the regression algorithm of the analysis model, the number of the samples in the training set, or the regression algorithm of the analysis model and the number of the samples in the training set, to resume training the analysis model via the training set, and to validate the resumed trained analysis model via the validation set to resume generating a predicted accuracy of the resumed trained analysis model until the predicted accuracy is not less than the preset threshold if the resumed predicted accuracy of the resumed trained analysis model is less than the preset threshold.

4. The method according to claim 1, wherein obtaining a plurality of sets of sample data comprises:
obtaining a plurality of sets of physiological measurements taken by the at least two uncalibrated measurement devices and a plurality of sets of standard physiological information measured by the at least two standard measurement devices;
combining the sets of physiological measurements and the sets of standard physiological information according to codes of the uncalibrated measurement devices and codes of the standard measurement devices to obtain a combination of each physiological measurement and all the standard physiological information, or a combination of each standard physiological information and all the physiological measurement.

5. The method according to claim 1, wherein the to-be-calibrated measurement devices comprises one or more of a group of a smart bracelet, smartwatch, a portable oximeter, and a portable scale.

6. An electronic device communicationally coupled to at least one to-be-calibrated measurement device, the electronic device comprising:
a storage device;
at least one processor; and
the storage device storing one or more programs, which when executed by the at least one processor, cause the at least one processor to:
obtain physiological reading collected by an uncalibrated measurement device;
input the reading into a model for calibration to generate a calibrated physiological measurement whereby a sub-module corresponding to the reading is called from the model for calibration and the sub-module is for calibrating the reading via a regression algorithm, where each sub-module in the model corresponds to one physiological reading;
output calibrated physiological measurement by the called sub-module;
further causing the at least one processor to:
select at least two regression algorithms selected from preset sorting algorithms, to train and to create at least two modules for a same kind of reading of the physiological state;
average the at least two created modules to generate the sub-module in the model for calibration;
further causing the at least one processor to:
obtain a plurality of sets of sample data, the sample data comprises physiological measurements of a user and standard physiological information, where the physiological measurements are taken by the at least one uncalibrated measurement device, and the standard physiological information is contained within or taken by the at least one standard measurement device;
divide the sample data into a training set and a validation set;
establish an analysis model based on a regression algorithm;
train the analysis model via the training set, where an input of the analysis model is the physiological measurements in the training set and an output of the analysis model is the standard physiological information in the training set;

validate the trained analysis model via the validation set to generate a predicted accuracy of the trained analysis model;

determine whether the predicted accuracy of the trained analysis model is less than a preset threshold;

determine the trained analysis model as being the module if the predicted accuracy of the trained analysis model is not less than the preset threshold.

7. The electronic device according to claim 6, further causing the at least one processor to:

compare the calibrated physiological measurement with a preset threshold range;

generate a prompt if the calibrated physiological measurement is outside of the preset threshold range.

8. The electronic device according to claim 6, further causing the at least one processor to:

adjust the regression algorithm of the analysis model, or the number of the samples in the training set, or the regression algorithm of the analysis model and the number of the samples in the training set, to resume training the analysis model via the training set if the predicted accuracy of the trained analysis model is less than the preset threshold;

validate the resumed trained analysis model via the validation set to resume generating a predicted accuracy of the resumed trained analysis model;

determine whether the resumed predicted accuracy of the resumed trained analysis model is less than the preset threshold;

determine the resumed trained analysis model as being the module if the resumed predicted accuracy of the resumed trained analysis model is not less than the preset threshold;

continue to adjust the regression algorithm of the analysis model, or the number of the samples in the training set, or the regression algorithm of the analysis model and the number of the samples in the training set, to resume training the analysis model via the training set, and to validate the resumed trained analysis model via the validation set to resume generating a predicted accuracy of the resumed trained analysis model until the predicted accuracy is not less than the preset threshold if the resumed predicted accuracy of the resumed trained analysis model is less than the preset threshold.

9. The electronic device according to claim 6, further causing the at least one processor to:

obtain a plurality of sets of physiological measurements taken by the at least two uncalibrated measurement devices and a plurality of sets of standard physiological information measured by the at least two standard measurement devices;

combine the sets of physiological measurements and the sets of standard physiological information according to codes of the uncalibrated measurement devices and codes of the standard measurement devices to obtain a combination of each physiological measurement and all the standard physiological information, or a combination of each standard physiological information and all the physiological measurement.

10. The electronic device according to claim 6, wherein the to-be-calibrated measurement devices comprises one or more of a group of a smart bracelet, smartwatch, a portable oximeter, and a portable scale.

11. A non-transitory storage medium storing a set of instructions, when the instructions being executed by at least one processor of an electronic device, causing the at least one processor to:

obtain physiological reading collected by an uncalibrated measurement device;

input the reading into a model for calibration to generate a calibrated physiological measurement whereby a sub-module corresponding to the reading is called from the model for calibration and the sub-module is for calibrating the reading via a regression algorithm, where each sub-module in the model corresponds to one physiological reading;

output calibrated physiological measurement by the called sub-module;

further causing the at least one processor to:

select at least two regression algorithms selected from preset sorting algorithms, to train and to create at least two modules for a same kind of reading of the physiological state;

average the at least two created modules to generate the sub-module in the model for calibration;

further causing the at least one processor to:

obtain a plurality of sets of sample data, the sample data comprises physiological measurements of a user and standard physiological information, where the physiological measurements are taken by the at least one uncalibrated measurement device, and the standard physiological information is contained within or taken by the at least one standard measurement device;

divide the sample data into a training set and a validation set;

establish an analysis model based on a regression algorithm;

train the analysis model via the training set, where an input of the analysis model is the physiological measurements in the training set and an output of the analysis model is the standard physiological information in the training set;

validate the trained analysis model via the validation set to generate a predicted accuracy of the trained analysis model;

determine whether the predicted accuracy of the trained analysis model is less than a preset threshold;

determine the trained analysis model as being the module if the predicted accuracy of the trained analysis model is not less than the preset threshold.

12. The non-transitory storage medium according to claim 11, further causing the at least one processor to:

compare the calibrated physiological measurement with a preset threshold range;

generate a prompt if the calibrated physiological measurement is outside of the preset threshold range.

13. The non-transitory storage medium according to claim 11, further causing the at least one processor to:

adjust the regression algorithm of the analysis model, or the number of the samples in the training set, or the regression algorithm of the analysis model and the number of the samples in the training set, to resume training the analysis model via the training set if the predicted accuracy of the trained analysis model is less than the preset threshold;

validate the resumed trained analysis model via the validation set to resume generating a predicted accuracy of the resumed trained analysis model;

determine whether the resumed predicted accuracy of the resumed trained analysis model is less than the preset threshold;

determine the resumed trained analysis model as being the module if the resumed predicted accuracy of the resumed trained analysis model is not less than the preset threshold;

continue to adjust the regression algorithm of the analysis model, or the number of the samples in the training set, or the regression algorithm of the analysis model and the number of the samples in the training set, to resume training the analysis model via the training set, and to validate the resumed trained analysis model via the validation set to resume generating a predicted accuracy of the resumed trained analysis model until the predicted accuracy is not less than the preset threshold if the resumed predicted accuracy of the resumed trained analysis model is less than the preset threshold.

14. The non-transitory storage medium according to claim 11, further causing the at least one processor to:

obtain a plurality of sets of physiological measurements taken by the at least two uncalibrated measurement devices and a plurality of sets of standard physiological information measured by the at least two standard measurement devices;

combine the sets of physiological measurements and the sets of standard physiological information according to codes of the uncalibrated measurement devices and codes of the standard measurement devices to obtain a combination of each physiological measurement and all the standard physiological information, or a combination of each standard physiological information and all the physiological measurement.

* * * * *